US009945876B2

(12) United States Patent
Cohen et al.

(10) Patent No.: US 9,945,876 B2
(45) Date of Patent: Apr. 17, 2018

(54) DIAGNOSTIC TOOLS FOR CHARCOT-MARIE-TOOTH DISEASE

(71) Applicant: PHARNEXT, Issy les Moulineaux (FR)

(72) Inventors: Daniel Cohen, Saint Cloud (FR); Ilya Chumakov, Vaux-le-Penil (FR); Serguei Nabirochkin, Chatenay-Malabry (FR)

(73) Assignee: PHARNEXT, Issy les Moulineaux (FR)

(*) Notice: Subject to any disclaimer, the term of this patent is extended or adjusted under 35 U.S.C. 154(b) by 0 days.

(21) Appl. No.: 14/755,466

(22) Filed: Jun. 30, 2015

(65) Prior Publication Data

US 2015/0301069 A1    Oct. 22, 2015

Related U.S. Application Data

(63) Continuation-in-part of application No. 13/510,700, filed as application No. PCT/EP2010/067855 on Nov. 19, 2010, now Pat. No. 9,494,605.

(30) Foreign Application Priority Data

Nov. 20, 2009    (EP) ..................... 09306121

(51) Int. Cl.
| G01N 33/92 | (2006.01) |
|---|---|
| A61K 31/485 | (2006.01) |
| A61K 31/197 | (2006.01) |
| A61K 31/047 | (2006.01) |

(52) U.S. Cl.
CPC ........... *G01N 33/92* (2013.01); *A61K 31/047* (2013.01); *A61K 31/197* (2013.01); *A61K 31/485* (2013.01); *G01N 2800/285* (2013.01); *G01N 2800/52* (2013.01)

(58) Field of Classification Search
CPC ............. G01N 33/92; G01N 2800/285; G01N 2800/52; G01N 280/52; A61K 31/486; A61K 31/197; A61K 31/047
See application file for complete search history.

(56) References Cited

U.S. PATENT DOCUMENTS

| 4,186,251 A | 1/1980 | Tarbutton |
|---|---|---|
| 7,060,452 B2 | 6/2006 | Rothblat et al. |
| 2003/0032001 A1* | 2/2003 | Broderick .......... A61B 5/14542 435/4 |
| 2008/0057509 A1 | 3/2008 | Lupski et al. |
| 2008/0171080 A1 | 7/2008 | Schaebitz et al. |
| 2009/0170072 A1 | 7/2009 | Mink et al. |
| 2010/0196907 A1* | 8/2010 | Semizarov .......... C12Q 1/6886 435/6.18 |

FOREIGN PATENT DOCUMENTS

| GB | 1429525 | 3/1976 |
|---|---|---|
| JP | 2005-314256 | 11/2005 |
| KR | 10-2007-0062480 | 6/2007 |
| WO | WO 1992/21694 | 12/1992 |
| WO | WO 2007/094027 | 8/2007 |
| WO | WO 2009/068668 | 6/2009 |
| WO | WO 2009068668 A1 * | 6/2009 ........... A61K 31/197 |

OTHER PUBLICATIONS

Nobbio et al., Impaired Expression of Ciliary Neurotrophic Factor in Charcot-Marie Tooth Type 1A Neuropathy, 68)5), 2009, 441-45.*
Plaitakis et al., Neurological disorders associated with deficiency of glutamate dehydrogenase. Ann Neurol 15:144-153, 1984.*
Quest Diagnostics, Amino Acid Analysis, 2011, retrieved from https://web.archive.org/web/20120912034953/http://www.questdiagnostics.com/testcenter/testguide.action?dc=TS_AminoAcidAnal on May 13, 2016, pp. 1-5 at 1.*
Genova Diagnostics, 2004, 10 pages, retrieved from http://www.homeopathicdoctor.ca/GSDL/App_Guides/Nuti/ag_aa.pdf on May 13, 2016 at 1-3.*
CMT, care of feet, retrieved from https://web.archive.org/web/20071113161035/http://cmt.org.uk:80/index.php?option=com_content&task=view&id=26&Itemid=71 on May 25, 2017, 2 pages.*
CMT, Exercise, retrieved from https://web.archive.org/web/20071113162147/http://cmt.org.uk:80/index.php?option=com_content&task=view&id=30&Itemid=67 on May 25, 2017, 3 pages.*
Patroclo, C. B. et al. "Autosomal Dominant HMSN with Proximal Involvement" *Arquivos De Neuro-Psiquiatria*, 2009, pp. 892-896, vol. 67, No. 3B.
Yao, J. K. et al. "Lipid Abnormalities in Hereditary Neuropathy, Part 2: Serum Phospholipids" *Journal of the Neurological Sciences*, 1978, pp. 225-236, vol. 36.
Niebroj,-Dobosz, I. et al. "Serum lipids in some polyneuropathies" *Neurologia I Neurochirurgia Polska*, 1977, pp. 421-426, vol. 27, No. 4.
Swartz, G. et al. "Antibodies to cholesterol" *Proceedings of the National Academy of Sciences USA*, Mar. 1988, pp. 1902-1906, vol. 85.

(Continued)

*Primary Examiner* — Andrea S Grossman
(74) *Attorney, Agent, or Firm* — Saliwanchik, Lloyd & Eisenschenk

(57) ABSTRACT

The present invention relates in particular to methods of detecting predisposition to or diagnosis and/or prognosis of Charcot-Marie-Tooth disease (CMT) and related disorders. More specifically, the invention relates to development, validation and application of new biomarkers which can be used for detecting the presence or risk of CMT disease and related disorders. In particular, the present invention relates to metabolite, lipid, carbohydrate and proteinaceous biomarkers that can be measured in biological body fluids and easily available extracts of biopsies, which can be used to aid in the detection, prediction of drug treatment and follow-up of this treatment of neurodegenerative disorders, including CMT disease. The present invention also relates to methods for identification of CMT disease subtypes and assessing the responsiveness to treatments and the efficacy of treatments in subjects having CMT or a related disorder.

12 Claims, 1 Drawing Sheet

(56) References Cited

OTHER PUBLICATIONS

XP007912053, "Charcot-Marie-Tooth Disease" pp. 1-8, retrieved from the internet: http://en.wikipedia.org/wiki/charcot-Marie-tooth_disease>, retrieved on Mar. 4, 2010.
Conrads, T. P. et al. "Sampling and analytical strategies for biomarker discovery using mass spectrometry" *BioTechniques,* Jun. 2006, pp. 799-805, vol. 40.
McLeod, J.G. et al. "Investigation of peripheral neuropathy" *Journal of Neurology, Neurosurgery, and Psychiatry,* 1995, pp. 274-283, vol. 58.
Giambonini-Brugnoli, G., et al. "Distinct disease mechanisms in peripheral neuropathies due to altered peripheral myelin protein 22 gene dosage or a Pmp22 point mutation" *Neurobiology of Disease,* 2005, pp. 656-668, vol. 18.
Yao, J. K. et al. "Lipid Abnormalities in Hereditary Neuropathy, Part 4: Endoneurial and Liver Lipids of HMSN-III (Dejerine-Sottas Disease)" *Journal of the Neurological Sciences,* 1981, pp. 179-190, vol. 52, Nos. 2-3.

\* cited by examiner

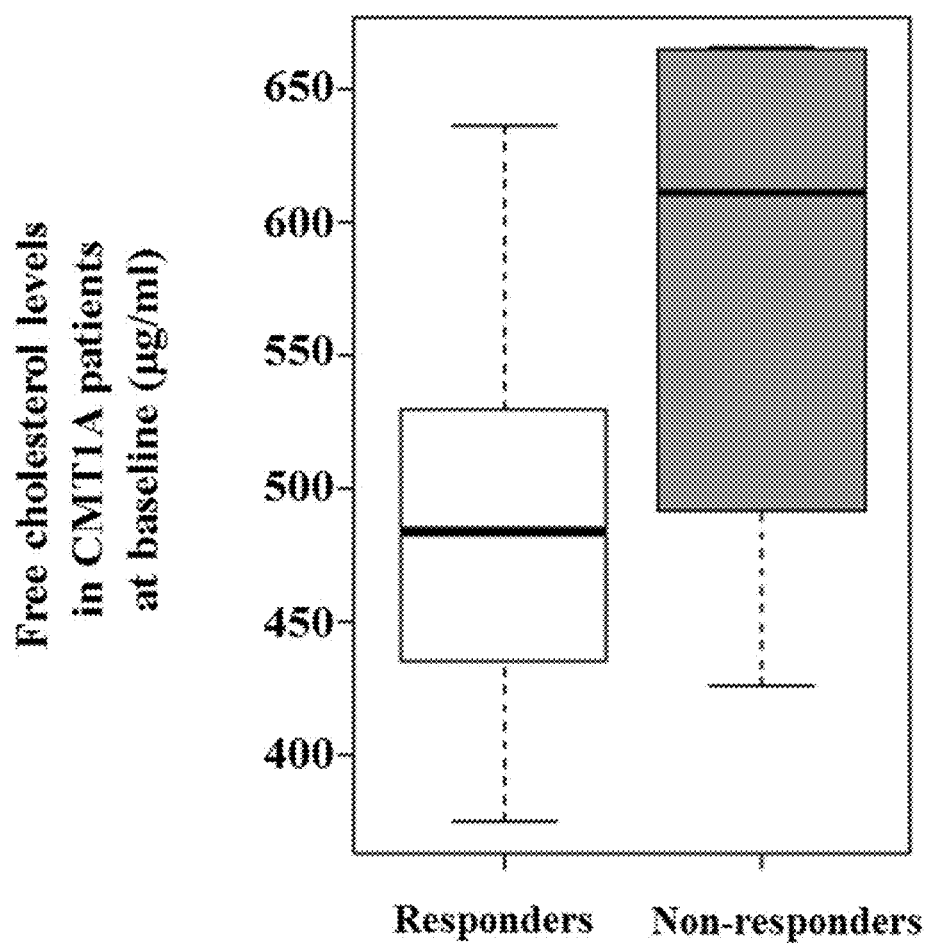

DIAGNOSTIC TOOLS FOR CHARCOT-MARIE-TOOTH DISEASE

CROSS-REFERENCE TO RELATED APPLICATIONS

This application is a continuation-in-part of co-pending application U.S. Ser. No. 13/510,700, filed Dec. 5, 2012, which is the U.S. national stage of International Patent Application No. PCT/EP2010/067855, filed Nov. 19, 2010.

The present invention relates generally to the field of medicine. The present invention relates in particular to methods of detecting predisposition to or diagnosis and/or prognosis of Charcot-Marie-Tooth (CMT) and related disorders. More specifically, the invention relates to development, validation and application of new biomarkers, which can be used for detecting the presence or risk of CMT disease and related disorders. In particular, the present invention relates to metabolite, lipid, carbohydrate and proteinaceous biomarkers that can be measured in biological body fluids and easily available extracts of biopsies, which can be used to aid in the detection, prediction of drug treatment and follow up of this treatment of neurodegenerative disorders, including CMT disease. The present invention also relates to methods for identification of CMT disease subtypes, and assessing the responsiveness to the treatments and the efficacy of treatments in subjects having CMT or a related disorder.

Charcot-Marie-Tooth disease ("CMT") is an orphan genetic peripheral polyneuropathy. Affecting approximately 1 in 2,500 individuals, this disease is the most common inherited disorder of the peripheral nervous system. Its onset typically occurs during the first or second decade of life, although it may be detected in infancy. The course of the disease is chronic with gradual neuromuscular degeneration. The disease is invalidating with cases of accompanying neurological pain and extreme muscular disability. CMT is one of the best studied genetic pathologies with approximately 30,000 cases in France. While a majority of CMT patients harbour a duplication of a chromosome 17 fragment containing a myelin gene, PMP22 (form CMT1A), more than two dozen genes have been implicated in different forms of CMT. Accordingly, although monogenic in origin, this pathology manifests clinical heterogeneity due to possible modulator genes. The genes mutated in CMT patients are clustered around tightly connected molecular pathways affecting differentiation of Schwann cells or neurons or changing interplay of these cells in peripheral nerves.

At present, the diagnosis of CMT disease is based on clinical criteria and electrophysiology data that distinguish only few subtypes of this disease. More precise classification relies on mutation analysis in relevant genes if known.

The multiple mutations leading to CMT disease occur in more than 25 different genes. They are not identified for all cases of CMT disease and cannot be exhaustingly classified by genetic typing (Suter & Scherer, 2003; Berger et al., 2006; Niemann et al., 2006; Nave et al., 2007). Moreover, clinical heterogeneity does occur and is not only important for clinical characterization but provides further implication of specific management/treatment for functionally different forms (Sereda et al., 2003; Passage et al., 2004; Sahenk et al., 2005; Young et al., 2008).

For the moment, no drug treatment exists for this disease but some clinical management procedures have been described (Grandis & Shy, 2005; Kapur et al., 2007; Weiner et al., 2008) and clinical trials with ascorbic acid for the treatment of the CMT1A form of this disease are under way (Burns et al., 2009).

A specific tool to measure the stage of the disease is CMT Neuropathy Score (CMTNS, Shy et al. 2005). CMTNS is used to measure patient disability in CMT patients and as an outcome measurement in treatment trials. It is a composite score gathering the results of symptoms, signs, and neurophysiological tests. Patients are classified as mild (CMTNS≤10), moderate (CMTNS 11-20), or severe (CMTNS>20) depending of their performances assessed in nine tests.

The Overall Neuropathy Limitations Scale (ONLS), though not specifically designed for CMT, is used to record serial changes in limitations in a clinical environment and as an outcome measure in clinical trials for patients suffering from neuropathies. It measures limitations in the everyday activities of the upper and lower limbs (Graham and Hughes, 2006).

The progression of this disease measured by CMTNS or ONLS is rather slow and necessitates long clinical trials with hundreds of patients.

The protein and RNA levels of PMP22 have been recently proposed as biological markers to follow up such trials pharmacodynamically as a substitute for CMTNS endpoint in a case of CMT1A (Li et al., 2005; Meyer zu Horste et al., 2007). Still, such analysis is tedious and requires invasive procedures. Moreover, expression of PMP22 in such biopsies is not correlated with severity of disease (Katona et al., 2009).

Patrocolo et al., 2009 reports elevated total cholesterol and triglyceride levels in a patient with Autosomal Dominant Hereditary Motor Sensory Neuropathy with Proximal Dominant Involvement (HMSN-P).

Yao et al., 1978 studies the distribution of specific fractions of cholesteryl esters in patients having hereditary neuropathies. This document provides no information regarding free cholesterol or LDL cholesterol levels.

Swartz et al., 1988 concerns immunogenicity of cholesterol and production of monoclonal IgM complement-fixing antibodies to cholesterol.

Niebroj-Dobosz et al., 1976 concerns patterns of different lipid fractions in neuropathic patients (such as total lipids, total phospholipids, free fatty acids or cholesterol esters). The authors conclude that there is no correlation between the type of lipid pattern changes and the clinical syndrome.

The availability of easily detectable biological markers would permit rapid diagnosis of functionally relevant forms of CMT and related diseases, clinical testing of efficacy of new medications and monitoring the individual response of patients to drug treatment and disease management.

SUMMARY OF INVENTION

The purpose of the present invention is to provide novel methods for detecting predisposition to, or diagnosis and/or prognosis of CMT disease and related disorders, as well as for assessing the responsiveness to the treatments and/or the efficacy of treatments in subjects having CMT or a related disorder.

As indicated herein, the present invention provides a method for the diagnosis of CMT and CMT-related diseases. The present invention also provides methods for aiding in the diagnosis and sub-classification of neurological disorders, or in patient stratification steps in clinical trials, including CMT and CMT-related diseases, by quantifying the amount of lipids, amino acids, steroid hormones, carbohydrates, metals, arachidonic acid metabolites, biogenic amines, nucleosides, nucleotides, small peptides and proteins in a biological fluid sample of the subject, such as cerebrospinal fluid, serum, saliva, urine, etc. and comparing the measured amount with a reference value for the biomarker. These methods can also be applied to quantification of biomarkers in extracts of biopsies including skin biopsies. The information thus obtained may be used to aid in the diagnosis, to diagnose the disease, or to predict potential drug response in the individual. The biomarkers are differentially present in subjects having a neurological disease, including CMT and CMT-related diseases, versus subjects free of the disease.

One embodiment of the present invention is a method of diagnosing or assessing the likelihood that a patient is afflicted with a neurological disease, including CMT, preferably CMT1A, and CMT-related diseases, the method comprising measuring a level of complex combination biomarkers of the present invention.

The present invention more specifically relates to an in vitro method for detecting the presence or risk of CMT disease in a mammal, or for aiding in the diagnosis, prognosis or sub-classification of CMT disease, or in patient stratification steps in clinical trials, the method comprising determining the (relative) amount or the presence, absence or alteration of a target biomarker in a biological fluid sample from the subject, wherein said amount or alteration is indicative of the presence, risk, progression or severity of said disease, and wherein said biomarker is selected from lipids, amino acids, steroid hormones, metals, metabolites of arachidonic acid, biogenic amines, carbohydrates, peptides, nucleosides and nucleotides.

The present invention also relates to an in vitro method for assessing efficacy of a treatment against CMT in a mammal, the method comprising determining in a biological fluid sample from the subject, during the treatment, the (relative) amount or the presence, absence or alteration of a target biomarker selected from lipids, amino acids, steroid hormones, metals, metabolites of arachidonic acid, biogenic amines, carbohydrates, peptides, nucleosides and nucleotides, and comparing said amount or alteration to a level of said biomarker determined before treatment or at an earlier stage of treatment in said mammal, wherein a deviation is indicative of the efficacy of the treatment.

The methods of the invention may use one or more target biomarker(s). In a preferred embodiment, said target biomarker(s) are selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin, or combinations thereof.

In another embodiment, said one or more biomarkers are used in conjunction with at least one additional diagnostic test or marker for CMT, preferably selected from nucleic acids, proteinous, physiological, neurophysiological, genetic, behavioral, electrophysiological, clinical and phenotypical tests or markers.

The present invention also relates to a use of one or more biomarker(s) of the present invention in a method of detecting predisposition to or diagnosis and/or prognosis of CMT disease in a mammalian subject.

A further particular object of the invention is to provide an in vitro method for predicting the responsiveness to a treatment of CMT disease of an individual suffering from CMT, the method comprising:
 i) determining the free cholesterol level in a biological sample from said individual, and ii) predicting the responsiveness of said individual to said treatment by comparing the free cholesterol level obtained in i) to a reference value of a responder or non-responder group.

The invention also provides, in a specific embodiment, an in vitro method for determining the progression of CMT disease in an individual having CMT, the method comprising:
 i) determining the level of alanine or tryptophan, or both, in a biological sample from said individual, and
 ii) comparing the level of alanine or tryptophan, or both, obtained in i) to level(s) of alanine and/or tryptophan, respectively, determined previously in the same individual,
 wherein a change in the level of alanine and/or tryptophan is indicative of the progression of CMT disease in said individual.

The invention also provides a method of partitioning a group of patients suffering from CMT disease comprising determining the levels of alanine or tryptophan, or both, in a biological sample from said patients, wherein said level(s) is/are used to partition said group of patients as a function of the severity of the disease.

BRIEF DESCRIPTION OF THE FIGURE

FIG. 1: Free cholesterol levels in CMT1A patients at baseline. Before the beginning of treatment with a mix of baclofen, naltrexone and sorbitol, free cholesterol levels were found to be significantly lower in patients who turned out to respond to the treatment, i.e., whose condition was stabilized or improved (responders, white box) in comparison with those who turned out to not respond to the treatment, i.e., whose condition worsened after one year of treatment (non-responders, grey box). (p<0.034, Welch's t-test, free cholesterol levels of responders significantly different from non-responders).

DETAILED DESCRIPTION OF THE INVENTION

The present invention provides new diagnostic methods and tools for CMT and related disorders.

Within the context of this invention, CMT includes CMT1A, CMT1B, CMT1C, CMT1D, CMT1X, CMT2A, CMT2B, CMT2D, CMT2E, CMT2F, CMT2I, CMT2J, CMT2-P0, CMT2K, CMT4A, CMT4B1, CMT4B2, CMT4C, CMT4D, CMT4F, CMT4, AR-CMT2A, CMT4J or other forms of Charcot-Marie-Tooth disease. In the most preferred embodiment, CMT is CMT1A.

Within the context of the present invention, the term "CMT-related disorder" designates other diseases associated with neurological symptoms. The term "CMT-related disorder" more particularly includes Alzheimer's disease (AD), senile dementia of AD type (SDAT), Parkinson's disease, Lewis body dementia, vascular dementia, autism, mild cognitive impairment (MCI), age-associated memory impairment (AAMI) and problems associated with aging, post-encephalitic Parkinsonism, schizophrenia, depression, bipolar disease and other mood disorders, Huntington's disease, motor neuron diseases including amyotrophic lateral sclerosis (ALS), multiple sclerosis, idiopathic neuropathies, diabetic neuropathy, toxic neuropathies including neuropathy induced by drug treatments, neuropathies provoked by HIV, radiation, heavy metal and vitamin deficiency states, prion-based neurodegeneration, including Creutzfeldt-Jakob disease (CJD), bovine spongiform encephalopathy (BSE), GSS, FFI, Kuru and Alper's syndrome.

The purpose of the present invention is to provide new body fluid biomarkers for diagnosing or monitoring CMT and related disorders, and for assessing the responsiveness of subjects or the efficacy of therapeutic treatments in subjects having CMT or a related disorder. Thus, according to a preferred embodiment, the method of the invention comprises the detection of the presence or absence or (relative) quantity of metabolites in body fluids.

An object of the invention resides in detecting (in vitro or ex vivo) the presence of or risk of developing CMT or a related disorder in a mammal, comprising the determination of the presence, in a biological sample of the mammal, of an alteration in one or more selected body fluid biomarkers.

Another object of the invention resides in a method for detecting (in vitro or ex vivo) the presence of or risk of developing CMT or a related disorder in a mammal, comprising the determination of the presence, in a biological sample of the mammal, of an alteration of the level in one or more markers, the presence of such an alteration being indicative of the presence of or risk of developing CMT in said mammal.

In a preferred embodiment, a method of the invention is an in vitro method for detecting the presence or risk of CMT disease in a mammal, or for aiding in the diagnosis, prognosis or sub-classification of CMT disease, or aiding in patient stratification steps in clinical trials, the method comprising determining the (relative) amount or the presence, absence or alteration of a target biomarker in a biological fluid sample from the subject, wherein said amount or alteration is indicative of the presence, risk, progression or severity of said disease, and wherein said biomarker is selected from lipids, amino acids, steroid hormones, metals, metabolites of arachidonic acid, biogenic amines, carbohydrates, peptides, nucleosides and nucleotides.

Within the context of the present invention, the term "alteration" of a target biomarker may designate an increase or a decrease of the target biomarker quantity in a fluid biological sample from the subject, in comparison with a control sample or reference value. Typically, the term "decrease" in relation to a biomarker level designates a reduction of the concentration or level of the biomarker in a biological sample from the subject of at least 5% or 10% or 15% in comparison with a control sample or reference or mean value. Decreases may be more substantial, such as a reduction by at least 20% or 30% or 40% or even more. Similarly, the term "increase" in relation to the biomarker level designates an augmentation of the concentration or level of the biomarker in a biological sample from the subject of at least 5% or 10% or 15% in comparison with a control sample or reference or mean value.

Increases may be more substantial, such as increases by at least 20% or 30% or 40% or even more.

Preferred types of alterations are disclosed below for each biomarker in Table A. This table indicates, for each biomarker, whether an increase or a decrease is indicative of CMT in human subjects. A distinction between male and female patients is also provided.

TABLE A

Increase (+) or decrease (−) of a biomarker concentration in CMT patients

|  | total | female | male |
|---|---|---|---|
| Adrenaline |  | − |  |
| Alanine | − | − |  |
| Alpha Amino Butyric acid |  | − |  |
| Citrulline |  |  | − |
| Cystine | − |  |  |
| Dopamine | + |  |  |
| Free cholesterol | − | − | − |
| Glutamine | − | − |  |
| Hydroxyproline | − | − |  |
| Iron | + |  |  |
| LDL cholesterol |  |  | − |
| LTB4 |  | − |  |
| Lysine |  | − |  |
| Methionine |  |  | + |
| Proline |  |  | + |
| Serotonin | + |  |  |
| T4 | − |  | − |
| Testosterone |  |  | + |
| Threonine | − |  |  |
| Tryptophan | + |  | + |
| Tyrosine |  | − |  |

Specific examples of alterations of each target biomarker(s) according to the invention are shown in Tables 1-4 of the experimental part.

Another embodiment of the present invention comprises qualifying and sub-classifying a CMT disease, for example CMT1A, CMT1B, CMT1C, CMT1D, CMT1X, CMT2A, CMT2B, CMT2D, CMT2E, CMT2F, CMT2I, CMT2J, CMT2-P0, CMT2K, CMT4A, CMT4B1, CMT4B2, CMT4C, CMT4D, CMT4F, CMT4, AR-CMT2A, CMT4J or other forms of Charcot-Marie-Tooth disease or CMT-related disorders in a subject, comprising measuring sets of complex biomarkers of the present invention.

In other aspects, methods of the present invention further comprise the step of managing the individual treatment. For example, if measurement of the set of biomarkers correlates with the presence of clinical subtype CMT disease, then managing treatment comprises administering a matched drug or drug combination to slow or revert the progression of the disease. Further measurements can be compared to the previous measurements or the standard to monitor the progression of the disease.

In another aspect of the invention, the method further comprises measuring the biomarker after treatment has begun, to monitor the progression of the disease.

In another embodiment, the method of the present invention comprises monitoring the progression of CMT, preferably CMT1A, and measuring a level of sets of biomarkers of the present invention.

Another object of the invention relates to a method to evaluate or follow the response to a treatment for CMT in a subject, the method comprising a step of measuring the level of one or more markers, the presence of such an alteration before and/or during the treatment, and a comparison of the level thus measured with that measured at a former stage of the treatment or before treatment.

Another object of the invention relates to a method to evaluate or follow the response to a treatment of CMT in a subject, the method comprising a step of measuring the amount of one or more selected body fluid biomarkers before and/or during the treatment, and a comparison of the amount thus measured with that measured at a former stage of the treatment or before treatment.

The level of the biomarker(s), measured according to the method of the present invention, is correlated with neurological disease, preferably CMT disease. In preferred embodiments, this may be accomplished by comparing the measured amount to a reference value for the biomarker(s). The reference value can be obtained by measuring an amount of the biomarker(s) in age-matched control subjects that are not affected by the disease, or that are free of the disease.

Another object of the invention relates to an in vitro method for assessing efficacy of a treatment against CMT in a mammal, the method comprising determining in a biological fluid sample from the subject, during the treatment, the (relative) amount or the presence, absence or alteration of a target biomarker selected from lipids, amino acids, steroid hormones, metals, metabolites of arachidonic acid, biogenic amines, carbohydrates, peptides, nucleosides and nucleotides, and comparing said amount or alteration to a level of said biomarker determined before treatment or at an earlier stage of treatment in said mammal, wherein a deviation is indicative of the efficacy of the treatment.

Another embodiment of the present invention comprises monitoring the efficacy of a treatment method of CMT, comprising measuring a level of a complex set of biomarkers of the present invention. In embodiments, the efficacy of treatment is measured by monitoring levels of the biomarkers in the subject compared to a reference, and/or compared to other previous tests of the subject or to an earlier stage of treatment/disease in the subject.

Another object of the invention relates to an improvement in methods of treating CMT or related disorders, the improvement consisting of measuring the level of expression of one or, preferably, several biomarkers before and/or during the treatment. The measurement of the level of biomarker expression makes it possible to adapt the treatment according to the evolution of pathology and/or efficacy of the treatment.

In a preferred embodiment, diagnosing or monitoring CMT and related disorders comprises the determination of the quantity (or the presence or absence), in a biological sample of the mammal, of said body fluid biomarker(s) selected from lipids, amino acids, steroid hormones, carbohydrates, metals, metabolites of arachidonic acid, biogenic amines, nucleosides, nucleotides, small peptides and proteins.

In a preferred embodiment, the method of the invention comprises the determination of the quantity (or the presence or absence), in a biological fluid sample of the mammal, of one or more body fluid biomarkers, wherein said body fluid biomarkers are selected from:
lipids, preferably cholesterol and its metabolites, including dehydroepiandrosterone (DHEA), and including more preferably free cholesterol or LDL cholesterol, or their amount in regard to total cholesterol,
amino acids or their derivatives, preferably including alanine, a amino butyric acid, citrulline, cystine, glutamine, hydroxyproline, lysine, methionine, proline, threonine, tryptophan, tyrosine, arginine, asparagine, aspartic acid, glutamic acid, glycine, histidine, 1-methyl histidine, isoleucine, leucine, ornithine, phenylalanine, serine, taurine and valine,
steroid hormones and their precursors or derivatives, preferably including T3 and T4 thyroid hormones, testosterone, 5α-dihydroprogesterone, allopregnanolone and corticosterone,
metals, preferably iron and zinc,
metabolites of arachidonic acid, preferably including leukotrienes (e.g., LTB4/5), prostaglandin PGE2, prostacyclin PGI2 and tromboxanes TXA2 and TXB2,
biogenic amines, preferably including adrenaline, dopamine and serotonin,
carbohydrates, preferably sorbitol,
nucleotides, preferably 3'-5'-cyclic adenosine monophosphate (cAMP), and
any combination thereof.

More preferably, said body fluid biomarkers are selected from:
lipids, preferably cholesterol and its metabolites, including free cholesterol or LDL cholesterol, or their amount in regard to total cholesterol,
amino acids or their derivatives, preferably including alanine, a amino butyric acid, citrulline, cystine, glutamine, hydroxyproline, lysine, methionine, proline, threonine, tryptophan and tyrosine,
steroid hormones, preferably including T4 thyroid hormone and testosterone,
metals, preferably iron,
metabolites of arachidonic acid, preferably including leukotrienes (e.g., LTB4/5),
biogenic amines, preferably including adrenaline, dopamine and serotonin, and
any combination thereof.

In another preferred embodiment, the method of the invention comprises the determination of the quantity (or the presence or absence), in a biological fluid sample of the mammal, of one or more body fluid biomarkers, wherein said body fluid biomarkers are selected from:
cholesterol metabolites, preferably including an ester of cholesterol, 27-hydroxycholesterol, pregnenolone, pregnenolone sulfate, and dehydroepiandrosterone sulfate (DHEAS),
steroid hormones and their precursors or derivatives, preferably including cortisol, cortisone, aldosterone, androstanediol, androstenedione, estradiol and estrone,
metabolites of arachidonic acid, preferably including prostaglandins PGD2 and PGF2α, 12-hydroxyeicosatetraenoic acid (12-HETE) and lipoxins (LXA4 and LXB4),
inositol and its derivatives, preferably including inositol monophosphates, phosphatidylinositol 3-phosphate [PI3P] and phosphatidylinositol (3,5)-bi-phosphate [PI(4,5)P2],
sphingolipids or phospholipids or their derivatives, preferably including lysophosphatidic acid, phosphatidic acid and sphingosine-1-phosphate (S1P),
endocannabinoids, preferably including arachidonoylethanolamine, 2-arachidonoyl glycerol, 2-arachidonyl glyceryl ether, N-arachidonoyl-dopamine and virodhamine, and
any combinations thereof.

In another preferred embodiment, a method of the invention comprises determining in a biological fluid sample from the subject the (relative) amount or the presence, absence or alteration of a target biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin, as well as any combinations thereof.

In a preferred embodiment, the biomarker used in the invention is or comprises at least cholesterol, more preferably free cholesterol, and/or LDL cholesterol and/or their amount in regard to total cholesterol. Within the context of the present invention the term "LDL cholesterol" designates all forms of cholesterol contained in LDL, including non-esterified cholesterol.

As shown in the experimental part, the inventors have surprisingly discovered that the level of free cholesterol or the level of LDL cholesterol decreases in diseased animals.

Thus, in the most preferred embodiment, the method of the invention comprises determining a decrease of free cholesterol and/or LDL cholesterol and/or their amount in regard to total cholesterol in a biological fluid sample from the subject, wherein said decrease of free cholesterol and/or LDL cholesterol and/or their amount in regard to total cholesterol is indicative of the presence, risk, progression or severity of the disease.

In a particular embodiment, the method of the invention comprises determining in a biological fluid sample from the subject a decrease of the ratio of free cholesterol to total cholesterol.

In another particular embodiment, the method of the invention comprises determining a decrease of the ratio of LDL cholesterol to total cholesterol.

As indicated, the method may comprise the determination of several biomarkers, e.g., 2, 3, 4, 5 or even more. These may be determined simultaneously or sequentially in a biological fluid sample.

In a particular variant, the presence or the absence or the (relative) quantity of at least three biomarkers is determined simultaneously or sequentially in a biological fluid sample from the mammalian subject.

In another embodiment, the method of the invention comprises the determination of the presence or the absence or the (relative) quantity, in a biological sample of the mammal, of at least four distinct biomarkers.

In another embodiment, the sets of biomarkers used in methods of the invention are selected from Table 5.

In a preferred embodiment, the sets of biomarkers comprise:
  free cholesterol and alanine;
  free cholesterol and T4 and tryptophan and hydroxyproline;
  free cholesterol and hydroxyproline;
  free cholesterol and T4 and tryptophan;
  free cholesterol and T4 and serotonin;
  free cholesterol and T4 and hydroxyproline;
  free cholesterol and T4; or
  free cholesterol and serotonin.

As illustrated in the examples, such sets of biomarkers are particularly efficient in predicting the presence of CMT disease. In particular, the results depicted in the examples show performances of 100% in training tests and between 78% and 100% in validation tests for these sets of biomarkers.

The level of said biomarker(s) may be determined by any methods known per se in the art, such as, without limitation, immunological methods, biochemical methods, chromatographic methods, enzymatic methods, cell-based assays, in vitro tests, etc. Examples of suitable methods are disclosed in the experimental section. The level of biomarker(s) determined may be compared to a reference value, a control, or a mean value, wherein a deviation from said value is indicative of the presence, risk, progression or severity of CMT. The deviation should typically be greater than 5%, more preferably 10%, even more preferably 15%.

Another aspect of the invention relates to a use of one or more biomarker(s) selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin in a method of detecting predisposition to or diagnosis and/or prognosis of CMT disease in a mammalian subject.

Also, as illustrated in the experimental part, the inventors have found that within a diseased population suffering from CMT, free cholesterol levels are also predictive of the responsiveness of a patient to a treatment for CMT. More particularly, the invention shows that, in a population of CMT patients that responds to a treatment with baclofen, naltrexone and sorbitol, free cholesterol levels are significantly lower than in a population that does not respond to such treatment.

Thus, in another preferred embodiment, the invention relates to an vitro method comprising identifying a patient more likely to respond to a treatment of CMT by measuring the free cholesterol level in said patient. Preferably, the method comprises comparing said free cholesterol level determined in a patient to a reference value of a non-responder or responder group, wherein said comparison allows determining the likelihood that the patient is a responder or non-responder. In a more particular embodiment, the method comprises comparing said free cholesterol level determined in a patient to a reference value of a non-responder group, wherein a significantly lower level of free cholesterol when compared to said reference value is indicative that the patient shall respond to the treatment.

As shown in the experimental part, the reference value of free cholesterol (in plasma) in a responder group is typically comprised between 446 and 520 µg/mL, more particularly between 446 and 483 µg/mL, even more particularly less than 483 µg/mL.

Accordingly, in a particular embodiment, the in vitro method comprises determining the free cholesterol level of said individual from a plasma sample obtained from the individual, wherein a free cholesterol level in said patient comprised between 446 and 520 µg/mL, more preferably between 446 and 483 µg/mL, even more preferably below 483 µg/mL, is indicative that the patient shall respond to said treatment. In a further embodiment, the in vitro method comprises comparing the plasma free cholesterol level of said patient with a reference value of a responder group with similar age, sex, condition, and/or any ongoing treatment (e.g., statin treatment).

As shown in the experimental part, the reference value of free cholesterol (plasma free cholesterol) in a non-responder group is typically greater than 520 µg/mL, even more particularly greater than 578 µg/mL.

Thus, in another embodiment, the in vitro method comprises determining the free cholesterol level in the plasma of said patient, wherein a free cholesterol level greater than 520 µg/mL, even more preferably greater than 578 µg/mL, is indicative that the patient will not respond to said treatment.

In a particular embodiment, the method allows determining responsiveness to a treatment of CMT comprising co-administering baclofen, naltrexone and sorbitol, or salts thereof, to said patient.

In a particular embodiment, the term "significantly lower" designates a level that is at least 5% lower, more preferably at least 10% lower, even more preferably at least 15% or more lower than the reference value.

In a particular embodiment, the biological fluid sample is a blood sample of the subject, preferably a plasmatic fraction from said subject.

In a particular embodiment, the above biomarkers are used in a method of detecting predisposition to, diagnosis and/or prognosis of CMT disease, or aiding in patient stratification steps in clinical trials, in conjunction with at least one additional diagnostic test or marker for CMT, selected preferably from proteinous, physiological, neurophysiological, genetic, behavioral, electrophysiological, clinical and phenotypical tests or markers.

In another particular embodiment, the level of said biomarker(s) used in a method of detecting predisposition to or diagnosis and/or prognosis of CMT disease, or aiding in patient stratification steps in clinical trials, is compared to a reference value wherein the deviation from said value is indicative of the presence, risk, progression or severity of CMT.

In more particular embodiments, said biomarkers used in a method for aiding in patient stratification steps in clinical trials or evaluating progression or severity of CMT comprise at least tryptophan (trp) and/or alanine (ala).

As shown in the experimental part, the inventors have surprisingly discovered that the variation of trp and/or alanine level(s) in CMT patients is correlated with the severity of the disease as determined by electrophysiological clinical tests or functional measures.

Accordingly, in a particular embodiment, the invention resides in an in vitro method for determining the progression of CMT disease in an individual having CMT, the method comprising:
  i) determining the level of alanine or tryptophan, or both, in a biological sample from said individual, and
  ii) comparing the level of alanine or tryptophan, or both, obtained in i) to level(s) of alanine or tryptophan, respectively, determined previously in the same individual,
  wherein a change in the level of alanine and/or tryptophan is indicative of the progression of CMT disease in said individual.

In a preferred embodiment, the method of the invention comprises determining an increase of trp and/or ala level(s) in a biological fluid sample from the subject in regard with previously determined level(s) in said patient, wherein said increase of trp and/or ala level(s) is indicative of an improvement of CMT disease.

In a particular embodiment, determining a level of trp and/or ala levels in a biological fluid sample from the subject is made in conjunction with at least one additional diagnostic test or marker for CMT, selected preferably from proteinous, physiological, neurophysiological, genetic, behavioral, electrophysiological, clinical and phenotypical tests.

In a preferred embodiment, determining the level of trp and/or ala level(s) in a biological fluid sample from the subject is made in conjunction with the determination of CMTNS and/or ONLS which are known to those skilled in the art.

In another preferred embodiment, determining the level of trp and/or ala level(s) in a biological fluid sample from the sample is made in conjunction with one or more of the assessments that compose CMTNS and/or ONLS which are well known to those skilled in the art.

In another preferred embodiment the method of the invention comprises determining the level(s) of trp and/or ala in biological fluid samples from a group of patients wherein said level(s) is/are used to partition said group of patients as a function of the severity of the disease.

In a particular embodiment the biological fluid sample is a blood sample of the subject, preferably plasma or a plasma fraction from said subject.

As shown in the experimental section, trp and/or ala level(s) is/are surprisingly found to vary as a function of the presence of a treatment of the disease which has been found to be effective in treating CMT. Indeed, in the course of a clinical trial for evaluating a mix of baclofen, naltrexone and sorbitol as a treatment for CMT disease, the inventors found that the level(s) of trp and/or ala were significantly higher in the treated population of patients when compared to patients administered with placebo, and this as soon as 3 months after the beginning of the treatment, whereas a disease evolution on such a short period cannot be determined using either CMTNS or ONLS.

In this regard a preferred embodiment of the invention is a method for assessing the response or responsiveness to a treatment of CMT, the method comprising measuring an increase of the level(s) of trp and/or ala in a biological fluid sample from a subject undergoing a treatment for CMT in regard to previously determined levels in said subject before the beginning of, or at an earlier stage of, said treatment, wherein said increase is indicative of a response to said treatment.

In a particular embodiment the time interval between the two measures is 2 months or more, preferably 2, 3, or 4 months.

In a more particular embodiment of the invention the method for assessing the response to a treatment of CMT comprises measuring an increase of level(s) of trp and/or ala in a biological fluid sample from a subject undergoing a treatment for CMT for 3 months, in regard to previously determined levels before the beginning of said treatment.

Typically, an increase in trp and/or ala level(s) greater than 5%, more preferably 10%, even more preferably 15% is indicative of a response to a treatment.

In an even more preferred embodiment the above method is used to assess the response to a combination treatment for CMT comprising the administration of baclofen, naltrexone and sorbitol.

In particular embodiment, any of the above mentioned body fluid biomarkers, or their combinations, can be used in conjunction with at least one additional diagnostic test or marker for CMT, preferably selected from nucleic acids, proteinous, physiological, neurophysiological, genetic, behavioral, electrophysiological, clinical and phenotypical tests or markers.

Said proteinous biomarkers, detectable in body fluids, which can be used for diagnosis of CMT, for monitoring the progression of CMT, or for monitoring the efficacy of CMT-relevant drugs, include NEFH neurofilament, p75/LNGFR nerve growth factor receptor, NTRK3 receptor, SCIP transcription factor, cyclin D1, lysosomal-associated membrane protein LAMP1, ATG7 autophagy related 7 homolog, proteasome activator subunits PSME1/2, PSMA1 proteasome subunit, ITGB1/4 integrins, insulin-like growth factor 1 (IGF1), insulin-like growth factor binding proteins 1/2/5 (IGFBP1/2/5), vitronectin (VTN), tenascins (TNC/R/XB), SCN10A voltage-gated sodium channel, KCNC1 potassium voltage-gated channel, aldose reductases including AKR1B1, sorbitol dehydrogenase (SORD), inositol (myo)-1(or 4)-monophosphatases IMPA1/2, ADP-ribosylation factor 6 (ARF6), calnexin (CANX), growth factors FGF2, PDGFA/B/C, VEGFA/B/C and TGFB1/2, neuregulins including NRG1, matrix metallopeptidase 2/9, tissue and urokinase plasminogen activators PLAT and PLAU, monocyte chemoattractant protein-1 (CCL2), leukemia inhibitory factor (LIF), interleukin 6, transferrin, and endogenous opioids POMC, PENK and PDYN as well as smaller peptides and other derivatives produced by metabolism of the above-mentioned molecules.

Additional protein biomarkers useful for diagnosis of Charcot-Marie-Tooth disease (CMT), for monitoring the progression of CMT, or for monitoring the efficacy of CMT-relevant drugs can be selected from peripheral myelin protein 22 PMP22, ciliary neurotrophic factor CNTF, fatty acid elongase ELOV16, glypican GPC3, myosins MYO1B/1G, phosphoprotein enriched in astrocyte PEA15, calcium binding proteins S100A3/4, troponins TNNT1/3 and ferritin FTH1 as well as smaller peptides and other derivatives produced by their metabolism.

Further protein biomarkers detectable in body fluids and useful for diagnosis of Charcot-Marie-Tooth disease, for monitoring the progression of CMT, or for monitoring the efficacy of CMT-relevant drugs can be selected from proteins or smaller peptides and their derivatives encoded by ATP1A1, FGL2, ACAT2, ACTN2, AK1, ANK3, ANXA1, APOD, CD151, CD24A, CD9, CD99, CETN2, CHN1, CLIC4, COL1A1/2, COL2A1, COL3A1, COL4A1, CRYAB, CTSC, CYBSB, CYB561, DEAF1, EMID1, EPB4.1L2, EZR, FASN, FBLN2, FDFT1, FHL1, FOS, GAPD, GATM, HBA1, HBB, IGF2, ITIH5, KIT, LGALS1, LPL, LXN, MAPK3, MFGE8, MGLL, MMP12, MRAS, MSLN, MTAP1B, NECL1, NPR3, ODF2, OGN, OLFM1, PCOLCE, PMM1, PROS1, PYGM, RAB2, RAP1GDS1, SERPINE2, SH3GL3, SIRT2, SPP1, TPM1/2, TUBA2 and UCHL1 genes.

The above groups of genes (or the corresponding proteins or ligands) represent valuable biomarkers which may be used, alone or in various combinations, to diagnose CMT or related disorders.

In still another aspect, the present invention provides a kit comprising a solid support comprising at least one capture agent attached thereto, wherein the capture agent binds or reacts with one or more component(s) of the biomarker protein complex of the present invention.

In a preferred embodiment, the kit of the invention comprises a solid support comprising at least one capture agent attached thereto, wherein the capture agent binds or reacts with at least one biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin. In a preferred embodiment, the kit of the invention comprises at least one compound binding to or reacting with at least one biomarker selected from cholesterol, alanine, α-aminobutyric acid, citrulline, cystine, glutamine, hydroxyproline, lysine, methionine, proline, threonine, tryptophan, tyrosine, T4 thyroid hormone, testosterone, iron, LTB4, adrenaline, dopamine and serotonin for the diagnosis, prognosis and/or for assessing the efficacy of a treatment or following the evolution of CMT1A disease.

The method of the invention is applicable to any biological sample of the mammal to be tested, in particular any sample comprising metabolites. Examples of such samples include blood, plasma, serum, saliva, urine, feces, tissue biopsy, etc. The sample can be obtained by any technique known in the art, for example by collection using, e.g., non-invasive techniques, or from collections or banks of samples, etc. The sample can in addition be pretreated to facilitate the accessibility of the target molecules, for example by lysis (mechanical, chemical, enzymatic, etc.), purification, centrifugation, separation, etc.

The invention is applicable to any mammal, preferably to a human.

Further aspects and advantages of this invention will be disclosed in the following experimental section, which shall be considered as illustrative only.

EXAMPLES

I. Identification of New Markers and Quantitation of Biomarkers

The invention discloses biomarkers of body fluids useful for the diagnosis, prognosis and/or for assessing the efficacy of a treatment or following the evolution of CMT disease.

I.1 CMT1A Transgenic Rat Model and Serum Sample Collection

The CMT transgenic rat model is a hemizygous PMP22 transgenic rat bearing three additional copies of mouse PMP22 gene and showing signs of demyelination in peripheral and cranial nerves (Sereda et al., 1996; Grandis et al., 2004). This CMT rat model is a good approximation of human CMT1A disease from a clinical point of view. Furthermore, the CMT rats already served as a model for an experimental CMT1A therapy (Meyer zu Hörste et al., 2007).

Inventors have looked for small molecules showing differential levels in wild-type and transgenic rats, thus constituting relevant biomarkers for CMT disease.

Except when otherwise specified, CMT1A model rats, four months old, are anaesthetized with ketamine (Imalgene) 100 mg/kg, ip. Blood is collected by cardiac puncture in two different tubes:

in one sterilized blood collection tube for coagulation; serum is collected and stored at −80° C.; and in one EDTA RNAse free tube; after centrifugation (+4° C.; 1260 g; 10 min), plasma is stored at −80° C.

I.2 Quantitation Methods

Free Cholesterol

Cholesterol was first extracted from samples with heptanes. Free cholesterol was further analyzed using a method adapted from Dong et al. (2007): cholest-4-en-3,6-dione formed from the oxidation of non-esterified cholesterol by the Jones oxidation was measured by HPLC/UV analyses. Stigmasterol was used as an internal standard.

Sorbitol

Proteins are first precipitated with ethanol. Sorbitol is analyzed mainly according the Dionex N°20 technical note, using anion exchange chromatography coupled with an electrochemical detector.

Metals

Quantitation of iron and zinc was performed by ICP/MS after mineralization of serum samples.

Arachidonic Acid Metabolites

Enzyme ImmunoAssays (EIA) kits from Cayman Chemical were used to analyze:

Prostaglandin $E_2$ (ref 514010)
Leukotriene $B_4$ (ref. 520111)
Thromboxane $B_2$ (ref. 519031)
6-keto Prostaglandine $F_{1\alpha}$ (ref. 515211)

Cyclic Adenosine Monophosphate

After precipitation of plasma proteins with ethanol, cAMP is analyzed with an EIA kit from Cayman Chemical (ref 581001) according the manufacturer's instructions.

Catecholamines

A solid phase extraction (SPE) was performed to concentrate and purify the samples. Adrenaline, dopamine, and serotoninserotonin were further analyzed by ion pair chromatography.

Amino Acids

Plasma proteins were precipitated with sulfosalicylic acid prior to analyzes. Derivatized amino acid quantitation was performed with a spectrophotometer after an automated cation exchange chromatography process.

Thyroid Hormones

Prior to the precipitation of plasma proteins with methanol, an internal standard was added to samples. Triiodothyronine (T3) and thyroxine (T4) were then quantified by an HPLC coupled to LC-MS/MS mainly according to Soukhova et al. (2004).

Neurosteroids

CMT1A model rats, four months old, were decapitated and blood was collected in two different tubes:

in one sterilized blood collection tube for coagulation; serum was collected and stored at −80° C.; and in one EDTA RNAse free tube; after centrifugation (+4° C.; 1260 g; 10 min), plasma was stored at −80° C.

Prior to analysis, plasma proteins were precipitated and neurosteroids were then purified and concentrated by SPE. Neurosteroids were further chemically derivatized with either 2-hydrozino-1-methylpyridine (to lower the detection threshold) (Higashi et al., 2005) or picolinic acid (Yamashita et al., 2007). According to the derivatization method, internal standard is $^2$H testosterone or $^2$H 3α-androstanediol. HPLC analysis of neurosteroids was coupled to a mass spectrometer. Searched neurosteroids and derivatives were aldosterone, pregnenolone sulfate, allopregnanolone, progesterone, 5α-dihydroprogesterone (DHP), 3α-androstanediol, testosterone, 5α dihydrotestosterone, DHEA and corticosterone.

Estrogens

Blood is collected as above. As for neurosteroids, estrone and estradiol are extracted from the sample with ethyl acetate prior to derivatization with picolinic acid purification and a concentration and purification step by SPE. $^2$H-estrone and $^2$H-17β-estradiol are used as internal standards.

I.3 Results

Duplicate samples were analyzed for each biomarker. Statistical analysis (Student's t-test, bilateral, type 3) comparing WT rats versus CMT1A (transgenic) rats was performed. Results are summarized in the three tables below. These tables report the mean level of biomarkers which present a notable difference (P<0.2) between WT and CMT1A rats in male and female (Table 1), in only male (Table 2) and in only female (Table 3).

The analysis of biomarkers has revealed that plasmatic free cholesterol level is significantly decreased in CMT1A male (P=0.05) and female (P=0.06) rats compared to WT rats. In females, our results displayed a significant decrease of alpha-aminobutyric acid (P=0.019), glutamine (P=0.025) and tyrosine (P=0.03) plasmatic levels versus controls.

Our results also show a significant decrease of the following biomarkers: alanine, cystine, glutamine, hydroxyproline, threonine, T4 thyroid hormone, citrulline, LTB4, adrenaline, and lysine; and a significant increase of the following biomarkers: tryptophan, testosterone, dopamine, serotonin, iron, methionine, and proline (Tables 1, 2 and 3).

I.4 Fluid Biological Samples Collection and Quantification Methods

Biomarkers of the invention can be easily quantified from other biological fluids. As an example quantitation from saliva samples is described by Karjalainen et al. (2007) for cholesterol, and by Syrjanen et al. (1990) for glutamine and tyrosine. Likewise, those small molecules can be quantified in urine as described elsewhere for cholesterol (Cenedella et al., 1981) and for amino acids (Venta et al., 2001).

TABLE 1

| biomarkers | WT MEAN | WT s.e.m. | TG MEAN | TG s.e.m. | P |
|---|---|---|---|---|---|
| Free cholesterol (µg/ml) | 144.82 | 4.18 | 118.45 | 3.96 | 0.0004 |
| Alanine (µmol/l) | 659.67 | 44.19 | 523.50 | 46.31 | 0.059 |
| Cystine (µmol/l) | 15.50 | 2.85 | 8.67 | 2.51 | 0.103 |
| Glutamine (µmol/l) | 792.00 | 60.46 | 694.50 | 18.11 | 0.174 |
| Hydroxyproline (µmol/l) | 54.00 | 4.41 | 41.33 | 6.31 | 0.135 |
| Threonine (µmol/l) | 295.00 | 20.30 | 258.17 | 15.76 | 0.184 |
| Tryptophan (µmol/l) | 79.83 | 4.76 | 93.00 | 3.94 | 0.060 |
| Dopamine (ng/ml) | 0.30 | 0.02 | 0.41 | 0.07 | 0.195 |
| Serotonin (ng/ml) | 112.50 | 22.82 | 406.05 | 133.26 | 0.079 |
| T4 (ng/ml) | 52.57 | 4.26 | 42.64 | 3.11 | 0.092 |
| Iron (µg/ml) | 4.77 | 0.45 | 7.03 | 1.24 | 0.134 |

TABLE 2

| | male | | | | |
|---|---|---|---|---|---|
| | WT | | TG | | |
| biomarkers | MEAN | s.e.m. | MEAN | s.e.m. | P |
| Free cholesterol (µg/ml) | 146.11 | 7.80 | 120.74 | 6.78 | 0.050 |
| Citrulline (µmol/l) | 109.00 | 9.29 | 92.00 | 3.61 | 0.201 |
| Methionine (µmol/l) | 49.67 | 2.73 | 55.67 | 1.76 | 0.150 |
| Proline (µmol/l) | 224.67 | 19.54 | 265.00 | 14.50 | 0.179 |
| Tryptophan (µmol/l) | 84.33 | 5.24 | 99.00 | 4.93 | 0.111 |
| Tyrosine (µmol/l) | 87.00 | 5.13 | 98.67 | 3.93 | 0.150 |
| Testosterone (ng/ml) | 1.81 | 0.40 | 3.37 | 0.85 | 0.201 |
| T4 (ng/ml) | 59.23 | 3.21 | 48.84 | 2.00 | 0.063 |

TABLE 3

| | female | | | | |
|---|---|---|---|---|---|
| | WT | | TG | | |
| biomarkers | MEAN | s.e.m. | MEAN | s.e.m. | P |
| Free cholesterol (µg/ml) | 143.54 | 4.41 | 116.16 | 4.88 | 0.006 |
| LTB4 (pg/ml) | 421.46 | 43.75 | 335.67 | 26.36 | 0.184 |
| Alanine (µmol/l) | 660.33 | 46.83 | 551.33 | 44.86 | 0.168 |
| Alpha Amino Butyric acid (µmol/l) | 13.33 | 1.33 | 6.67 | 0.88 | 0.019 |
| Glutamine (µmol/l) | 905.33 | 46.94 | 687.33 | 38.84 | 0.025 |
| Hydroxyproline (µmol/l) | 49.00 | 6.66 | 29.00 | 2.52 | 0.081 |
| Lysine (µmol/l) | 510.67 | 25.96 | 419.00 | 22.50 | 0.057 |
| Tyrosine (µmol/l) | 80.00 | 2.65 | 56.33 | 5.36 | 0.030 |
| Adrenaline (ng/ml) | 7.99 | 0.76 | 5.97 | 0.58 | 0.107 |

II. Identification and Quantitation of Other Cholesterol-Related Biomarkers

II.1 CMT1A Transgenic Rat Model and Serum Sample Collection

The CMT transgenic rat model and sample collection are the same as described above (see section I.1).

II.2 Cholesterol Quantitation Methods

Total Cholesterol

Total cholesterol has been determined by an enzymatic assay with ABX Pentra Cholesterol CP kit (Horiba). The cholesterol is consumed by cholesterol esterase and cholesterol oxidase in a color-forming reaction where the color produced is proportional to the amount of the total cholesterol present in the sample.

LDL Cholesterol

LDL cholesterol has been determined by an enzymatic assay with ABX Pentra LDL

Direct CP kit (Horiba). The method is in a two-reagent format and depends on the properties of the detergents used.

The first detergent solubilizes all the non-LDL lipoprotein particles. The cholesterol released is consumed by cholesterol esterase and cholesterol oxidase in a non-color-forming reaction. The second detergent solubilizes the remaining LDL particles and a chromogenic coupler allows for color formation. The enzyme reaction in the presence of the coupler produces color that is specifically proportional to the amount of LDL cholesterol present in the sample.

II.3 Results

Results presented in Table 4 below were extracted from independent assays and analysed with a bilateral Student's t-test comparing 20 WT rats versus 19 CMT1A (transgenic) rats.

TABLE 4

| Biomarkers | WT | | TG | | |
|---|---|---|---|---|---|
| | MEAN | s.e.m | MEAN | s.e.m | P |
| Total cholesterol | 1.81 | 0.07 | 1.77 | 0.05 | 0.66129 |
| LDL cholesterol | 0.26 | 0.02 | 0.21 | 0.01 | 0.03951 |

Our results show that LDL-cholesterol level is significantly decreased (P=0.039) in CMT1A rats (TG) compared to WT rats while total cholesterol level isn't significantly modified. LDL-cholesterol level is very easily quantifiable with commonly used detection kits.

Correlation of Biomarker Concentration with Results from Behavioral Tests, Histology, Gene Expression and Electrophysiology Motor performance and muscular strength, Sensory Nerve Action Potentials (SNAP), axonal diameter distribution and myelin sheath of fixed sciatic nerve, fiber content in fixed muscles and pmp22 mRNA expression were compared with biomarker amounts measured in biological fluids. The test used is a test of linear association between paired samples using Pearson's product moment correlation. It is a unilateral test and a significance threshold of 0.05 is applied on p-values.

Such analysis demonstrates that the levels of the biomarkers of the invention are correlated with some of the above-mentioned behavioral tests, histology, PMP22 gene expression and electrophysiology, confirming thereby the significance of those biomarkers in CMT1A physiology and the pertinence of the use of these biomarkers in the diagnosis and follow-up of CMT1A.

III. Identification of Disease Predictors from Biomarkers of the Invention

Statistical analysis of the level of biomarkers of the invention obtained in the above experiments shows that said biomarkers can also be used in different sets of grouped biomarkers to predict the presence of disease with a good score. Predictability scores are shown for some of the possible sets comprising several of the molecules identified herein as biomarkers for CMT disease Table 5).

Briefly, diagnosis of the disease was performed by applying a Linear Discriminant Analysis (LDA), commonly used in statistics, pattern recognition and machine learning to find a linear combination of features which characterize or separate two or more classes of objects. The LDA was implemented in R (r-project.org/).

The LDA algorithm was applied on several sets of biomarkers selected on the basis of their correlation to the trait of interest (here transgenic versus wild-type). In order to properly assess the performances of each set of biomarkers, groups of rats were split into an independent "training set" (75% of rats) on which LDA was trained, and a "validation set" (25% of rats), on which the trained algorithm was validated. To be homogeneous, training and validation sets were made of equal proportions of transgenic/wild-type and male/female rats. Since the level of biomarkers differs between males and females, for a given set of biomarkers, LDA was trained and validated separately on males and females. Finally the trained LDA was used to classify each rat of the training and validation sets into "wild-type" and "transgenic", and the proportion of rats that were well-classified allowed assessment of the performances of the algorithm. This procedure was reapplied iteratively in order to average the performances over all the possible samplings.

TABLE 5

| | Training | | | Validation | | |
|---|---|---|---|---|---|---|
| Biomarkers | Male | Female | Male and Female | Male | Female | Male and Female |
| Hydroxyproline and Alanine | 68% | 100% | 84% | 45% | 83% | 64% |
| Tryptophan and Hydroxyproline | 86% | 100% | 93% | 56% | 84% | 70% |
| T4 and Tryptophan and Hydroxyproline and Alanine | 92% | 100% | 96% | 60% | 89% | 75% |
| T4 and Hydroxyproline | 92% | 100% | 96% | 60% | 79% | 69% |
| T4 and Hydroxyproline and Alanine | 92% | 100% | 96% | 61% | 83% | 72% |
| Hydroxyproline and SerotoninSerotonin and Alanine | 81% | 100% | 90% | 61% | 84% | 72% |
| Hydroxyproline and SerotoninSerotonin | 74% | 100% | 87% | 61% | 72% | 67% |
| T4 and Tryptophan and Hydroxyproline | 94% | 100% | 97% | 61% | 89% | 75% |
| Tryptophan and Hydroxyproline and Alanine | 89% | 100% | 94% | 61% | 73% | 67% |
| Total of 20 biomarkers* | 100% | 100% | 100% | 62% | 72% | 67% |
| T4 and Tryptophan and Hydroxyproline and SerotoninSerotonin | 95% | 100% | 97% | 67% | 77% | 72% |
| Tryptophan and Hydroxyproline and SerotoninSerotonin and Alanine | 86% | 100% | 93% | 67% | 72% | 69% |
| T4 and Serotonin | 95% | 74% | 84% | 71% | 62% | 67% |
| Tryptophan and Hydroxyproline and Serotonin | 89% | 100% | 95% | 72% | 72% | 72% |

TABLE 5-continued

| | Training | | | Validation | | |
|---|---|---|---|---|---|---|
| Biomarkers | Male | Female | Male and Female | Male | Female | Male and Female |
| T4 and Tryptophan and Serotonin and Alanine | 92% | 95% | 93% | 72% | 77% | 75% |
| T4 and Tryptophan | 95% | 97% | 96% | 72% | 77% | 75% |
| T4 and Hydroxyproline and Serotonin and Alanine | 85% | 95% | 90% | 72% | 83% | 78% |
| T4 and Tryptophan and Alanine | 94% | 97% | 96% | 72% | 78% | 75% |
| T4 and Hydroxyproline and Serotonin | 91% | 100% | 96% | 73% | 71% | 72% |
| T4 and Alanine | 89% | 83% | 86% | 73% | 73% | 73% |
| T4 and Tryptophan and Hydroxyproline and Serotonin and Alanine | 94% | 100% | 97% | 73% | 83% | 78% |
| Serotonin and Alanine | 78% | 78% | 78% | 73% | 71% | 72% |
| T4 and Serotonin and Alanine | 86% | 78% | 82% | 73% | 71% | 72% |
| T4 and Tryptophan and Serotonin | 94% | 97% | 96% | 73% | 77% | 75% |
| Tryptophan and Alanine | 92% | 83% | 87% | 77% | 61% | 69% |
| Free-cholesterol and Hydroxyproline and Serotonin and Alanine | 100% | 100% | 100% | 78% | 78% | 78% |
| Free-cholesterol and Tryptophan and Hydroxyproline and Alanine | 100% | 100% | 100% | 78% | 84% | 81% |
| Free-cholesterol and Tryptophan and Hydroxyproline and Serotonin and Alanine | 100% | 100% | 100% | 78% | 72% | 75% |
| Free-cholesterol and Hydroxyproline and Alanine | 100% | 100% | 100% | 78% | 88% | 83% |
| Tryptophan and Serotonin | 86% | 82% | 84% | 78% | 66% | 72% |
| Free-cholesterol and Tryptophan and Hydroxyproline | 100% | 100% | 100% | 83% | 83% | 83% |
| Free-cholesterol and Tryptophan and Alanine | 100% | 100% | 100% | 84% | 72% | 78% |
| Tryptophan and Serotonin and Alanine | 83% | 84% | 83% | 84% | 72% | 78% |
| Free-cholesterol and Tryptophan and Serotonin and Alanine | 100% | 100% | 100% | 84% | 72% | 78% |
| Free-cholesterol and Hydroxyproline and Serotonin | 100% | 100% | 100% | 84% | 77% | 80% |
| Free-cholesterol and Tryptophan and Hydroxyproline and Serotonin | 100% | 100% | 100% | 84% | 73% | 79% |
| Free-cholesterol and Serotonin and Alanine | 100% | 100% | 100% | 84% | 79% | 81% |
| Free-cholesterol and T4 and Serotonin and Alanine | 100% | 100% | 100% | 88% | 78% | 83% |
| Free-cholesterol and T4 and Tryptophan and Alanine | 100% | 100% | 100% | 89% | 88% | 88% |
| Free-cholesterol and T4 and Hydroxyproline and Alanine | 100% | 100% | 100% | 89% | 90% | 89% |
| Free-cholesterol and T4 and Tryptophan and Serotonin and Alanine | 100% | 100% | 100% | 89% | 77% | 83% |
| Free-cholesterol and T4 and Tryptophan and Hydroxyproline and Serotonin and Alanine | 100% | 100% | 100% | 89% | 78% | 84% |
| Free-cholesterol and T4 and Tryptophan and Hydroxyproline and Alanine | 100% | 100% | 100% | 89% | 88% | 89% |
| Free-cholesterol and T4 and Hydroxyproline and Serotonin and Alanine | 100% | 100% | 100% | 89% | 78% | 84% |
| Free-cholesterol and T4 and Tryptophan and Hydroxyproline | 100% | 100% | 100% | 94% | 94% | 94% |
| Free-cholesterol and T4 and Hydroxyproline and Serotonin | 100% | 100% | 100% | 94% | 77% | 86% |
| Free-cholesterol and T4 and Tryptophan and Serotonin | 100% | 100% | 100% | 94% | 79% | 87% |
| Free-cholesterol and T4 and Alanine | 100% | 100% | 100% | 94% | 83% | 89% |
| Free-cholesterol and T4 and Tryptophan and Hydroxyproline and Serotonin | 100% | 100% | 100% | 94% | 77% | 86% |
| Free-cholesterol and Hydroxyproline | 100% | 100% | 100% | 94% | 94% | 94% |
| Free-cholesterol and Tryptophan and Serotonin | 100% | 100% | 100% | 95% | 67% | 81% |

TABLE 5-continued

|  | Training | | | Validation | | |
|---|---|---|---|---|---|---|
| Biomarkers | Male | Female | Male and Female | Male | Female | Male and Female |
| Free-cholesterol and Alanine | 100% | 100% | 100% | 95% | 89% | 92% |
| Free-cholesterol and T4 and Tryptophan | 100% | 100% | 100% | 95% | 89% | 92% |
| Free-cholesterol and Tryptophan | 100% | 100% | 100% | 95% | 78% | 86% |
| Free-cholesterol and T4 and Serotonin | 100% | 100% | 100% | 100% | 78% | 89% |
| Free-cholesterol and Serotonin | 100% | 100% | 100% | 100% | 79% | 89% |
| Free-cholesterol and T4 and Hydroxyproline | 100% | 100% | 100% | 100% | 95% | 97% |
| Free-cholesterol and T4 | 100% | 100% | 100% | 100% | 95% | 97% |

*Total of 20 biomarkers: Free Cholesterol, T4, Tryptophan, Hydroxyproline, Serotonin, Alanine, alpha-Aminobutyric acid, Citrulline, Cystine, Glutamine, Lysine, Methionine, Proline, Threonine, Tyrosine, Testosterone, Iron, LTB4, Adrenaline, Dopamine.

IV. Biomarker Analysis in CMT1A Patients

An analysis of blood biomarkers was performed as a secondary objective of a double-blind, randomized, placebo-controlled Phase 2 study (ClinicalTrials.gov Identifier: NCT01401257) of which the primary objective was to assess the clinical and laboratory safety and tolerability of three doses of a mix of baclofen, naltrexone and sorbitol (MIX), a candidate treatment administered orally for 12 months to CMT1A patients versus placebo.

Patients aged 18-65 years were included with CMT1A diagnosis based on clinical examination and confirmation by genotyping (duplication in 17p11.2), weakness in at least foot dorsiflexion, and a Charcot-Marie-Tooth Neuropathy Score (CMTNS)<20, i.e., mild to moderate severity. Eligible patients were randomly assigned in a 1:1:1:1 ratio to receive daily for one year Placebo, Low dose (LD=0.6 mg baclofen, 0.07 mg naltrexone and 21 mg sorbitol), Intermediate dose (ID=1.2 mg baclofen, 0.14 mg naltrexone and 42 mg sorbitol) or High dose (HD=6 mg baclofen, 0.7 mg naltrexone and 210 mg sorbitol) of the mix.

The results regarding the efficacy of the treatment of this Phase 2 study have been published (Attarian et al., 2014). Patients treated with the highest dose show consistent evidence of improvement beyond stabilization of the disease after one year of treatment.

IV.1 Biomarker Collection

Blood samples were taken both at randomization and after 3 months of treatment with the mix (3 doses tested) or placebo. Following sample collection in lithium-heparin, tubes were centrifuged for 10 min at 1300 g at room temperature, and plasma samples were stored at −80° C. until analysis.

Plasma concentrations were determined using HPLC coupled with Mass Spectrometry detection (LC-MS/MS) after protein precipitation for L-alanine and L-tryptophan and Liquid/Liquid extraction for free cholesterol.

The Lower Limits of Quantification (LLOQ) were 20 μg/mL, 10 μg/mL, and 5 μg/mL for free cholesterol, L-alanine, and L-tryptophan respectively. The results are expressed as μg/mL for L-alanine, free cholesterol and L-tryptophan.

IV.2 Efficacy Endpoints

The clinical endpoints considered in the trial are listed in Table 6:

TABLE 6

| Endpoints | Improvement (direction of variation for an improvement) | Reference/comments |
|---|---|---|
| *Clinical scales* | | |
| CMTNS | ↓ | Shy et al. (2005) |
| ONLS | ↓ | Graham and Hughes (2006) |
| *Functional measures* | | |
| 6MWT (m) | ↑ | Guyatt et al. (1985) |
| 9HPT (s) | ↓ | Hogrel et al. (2007) (non dominant hand considered) |
| Ankle Dorsiflexion (Nm) | ↑ | Hogrel et al. (2007) (mean of left and right side considered) |
| Grip (kg) | ↑ | Hogrel et al. (2007) (non dominant hand considered) |
| *Electrophysiological parameters* | | |
| CMAP (mV) | ↑ | measured from the mean sensory responses of the median and ulnar nerves (non-dominant side) |
| MCV (m/s) | ↑ | |

Compound muscle action potential (CMAP) is an electromyography investigation which represents the summation of a group of almost simultaneous action potentials from several muscle fibers in the same area which are evoked by stimulation of the motor nerve. Patients with impaired peripheral nerves show a decreased CMAP.

Motor conduction velocity (MCV) is the speed at which an electrical stimulation of a nerve propagates down to a muscle supplied by this nerve. Patients suffering from motor neuropathies display reduced speeds.

IV.3 Statistical Analysis

All analyses were performed on the Full Analysis Set (all randomized patients) using R version 3.1.2 (cran.r-project.org). Considering the exploratory nature of the study, statistical tests were conducted at a two-sided 5% level. Correlations were assessed using a Spearman's rank test. When specified, correlations were assessed based on data adjusted on Gender, Age and Centre with a linear model. Comparisons of two groups were performed using a Welch's t-test; comparisons of more than two groups were performed using an Analysis of Variance (ANOVA).

Effect of Treatment Analysis

Differences at 3 months between patients under baclofen, naltrexone and sorbitol mix treatment and patients under placebo were assessed by Analysis of Covariance (AN- COVA) adjusted on baseline values and also including gender, age and clinical centre as fixed covariates. The significance of the treatment effect on the combination of two biomarkers was assessed through the O'Brien's OLS test.

Identification of Responders

Biomarker levels at baseline between non-deteriorated patients (e.g., exhibiting improved or stabilized symptoms) and deteriorated (exhibiting a worsened condition) at 12 months following the approach of Attarian et al. (2014) on efficacy endpoints have been compared.

IV. 4 Results

Correlation Between Disease State or Evolution and Biomarkers

A baseline correlation analysis has been performed between efficacy endpoints and biomarkers by adjusting for gender, age and clinical centre in order to take into account any variation not related to the disease state.

The level of tryptophan is found to correlate significantly with all efficacy endpoints (Table 7). This correlation is positive with endpoints for which an increase means improvement and negative with endpoints for which a decrease means improvement. Consequently, higher tryptophan levels are found to be associated with less severe disease profiles.

Alanine also shows a correlation with some of the endpoints (Table 7).

Noteworthily, a significant and positive correlation between the two biomarkers (R=0.44, p=7e-05) is observed, which confirms the correlation to efficacy endpoints observed for both tryptophan and alanine.

TABLE 7

| Endpoints | Improvement (direction of variation for an improvement) | Spearman's coefficient correlation ($p < 0.05$) | |
|---|---|---|---|
| | | L-Trp | L-Ala |
| Clinical scales | | | |
| CMTNS | ↓ | −0.27 | ns |
| ONLS | ↓ | −0.29 | ns |
| Functional measures | | | |
| 6MWT (m) | ↑ | +0.4 | +0.3 |
| 9HPT (s) | ↓ | −0.25 | ns |
| Ankle Dorsiflexion (Nm) | ↑ | +0.36 | ns |
| Grip (kg) | ↑ | +0.26 | ns |
| Electrophysiological parameters | | | |
| CMAP (mV) | ↑ | +0.34 | +0.36 |
| MCV (m/s) | ↑ | +0.28 | +0.24 |

Of note, the efficacy endpoints correlate well and significantly with each other and in a coherent way with regard to the severity of the disease. Then, even if moderate, due to the multidimensional nature of the disease, efficacy endpoints and also variation of tryptophan and alanine bear a predictable relationship to the overall disease severity.

Hence, tryptophan and/or alanine level(s) can be used to assess the evolution and the severity of CMT1A in the patient population.

Biomarker Levels as Early Markers of the Efficacy of a Treatment

The effect of 3 months' treatment with baclofen, naltrexone and sorbitol on the biomarker levels was assessed (Table 8). A significant increase in tryptophan (p=0.018) and alanine (p=0.04) in patients treated for 3 months with the mix (1.56±2.98 µg/mL and 3.05±8.16 µg/mL respectively) compared to placebo (0.43±1.45 µg/mL and 0.75±6.75 µg/mL respectively) is found. When these two markers were considered jointly, the significance of the effect of treatment was even greater (p=0.0086). Noteworthily, after 3 months of treatment no symptomatic change is evidenced in the treated population, because of the slow and progressive nature of the disease. Biomarkers of the invention thus provide efficient tools to determine the response to a treatment.

TABLE 8

| | Placebo (n = 19) | | MIX HD (n = 19) | | MIX HD vs Placebo | |
|---|---|---|---|---|---|---|
| Biomarker | Baseline | Change from Baseline | Baseline | Change from Baseline | Estimate | p |
| Alanine (µg/ml) | 30.17 (6.80) | 0.75 (6.75) | 32.77 (11.55) | 3.05 (8.16) | 4.0 (0.19; 7.87) | 0.04* |
| Tryptophan (µg/ml) | 10.26 (2.19) | 0.43 (1.45) | 10.69 (1.75) | 1.56 (2.98) | 1.6 (0.29; 2.86) | 0.018* |

MIX: mix of baclofen, naltrexone and sorbitol; HD: High Dose of MIX (6 mg baclofen, 0.7 mg naltrexone and 210 mg sorbitol).
*data are mean changes from baseline (s.d.); Estimate: differences of change from baseline adjusted on Gender, Age and Centre, least squares mean (95% confidence interval). (ANCOVA, *p < 0.05).

Free Cholesterol Levels to Discriminate Responders from Non-Responders to Treatments of CMT Among patients treated with baclofen, naltrexone and sorbitol, those for which a worsening in their condition (non-responders) was observed after one year of treatment were found to have a significantly higher plasma concentration in free cholesterol than the responders (p=0.034) at the beginning of the study (FIG. 1). Hence biomarkers of the invention can be used as a predictor of the response or responsiveness to baclofen, naltrexone and sorbitol combination treatment.

BIBLIOGRAPHY

Attarian, S. et al. An Exploratory Randomised Double-Blind and Placebo-Controlled Phase 2 Study of a Combination of Baclofen, Naltrexone and Sorbitol (PXT3003) in Patients with Charcot-Marie-Tooth Disease Type 1A. Orphanet Journal of Rare Diseases (2014);9: 1-15.

Berger, P. et al. Schwann cells and the pathogenesis of inherited motor and sensory neuropathies (Charcot-Marie-Tooth disease). Glia. 2006; 54(4):243-257.

Burns, J. et al. Ascorbic acid for Charcot-Marie-Tooth disease type 1A in children: a randomised, double-blind, placebo-controlled, safety and efficacy trial. Lancet Neurol. 2009; 8(6):537-544.

Cenedella, R. J. et al. Studies on the source of urinary cholesterol in the normal human male. The Journal of Lipid Research. 1981; 22:122-130.

Dong, J. et al. Jones oxidation and high performance liquid chromatographic analysis of cholesterol in biological samples J. Chromatogr. B (2007);858:239-246.

Graham, R. C., and Hughes R. A. C. A Modified Peripheral Neuropathy Scale: The Overall Neuropathy Limitations Scale. Journal of Neurology, Neurosurgery, and Psychiatry (2006);77 (8): 973-76.

Grandis, M. et al. Early abnormalities in sciatic nerve function and structure in a rat model of Charcot-Marie-Tooth type 1A disease. Exp Neurol. (2004);190(1):213-23.

Grandis, M. & Shy, M. E. Current Therapy for Charcot-Marie-Tooth Disease. Curr Treat Options Neurol. 2005; 7(1):23-31.

Guyatt, G. H. et al. The 6-Minute Walk: A New Measure of Exercise Capacity in Patients with Chronic Heart Failure. *Canadian Medical Association Journal*. (1985);132 (8): 919-23.

Higashi, T. et al. 2-Hydrazino-1-methylpyridine: a highly sensitive derivatization reagent for oxosteroids in liquid chromatography-electrospray ionization-mass spectrometry. samples *J. Chromatogr. B* (2005);825:214-222.

Hogrel, J. Y. et al. Development of a French Isometric Strength Normative Database for Adults Using Quantitative Muscle Testing. Archives of Physical Medicine and Rehabilitation (2007) 88 (10): 1289-97. doi:10.1016/j.apmr.2007.07.011.

Kapur, S. et al. Anesthetic management of a parturient with neurofibromatosis 1 and Charcot-Marie-Tooth disease. J Clin Anesth. 2007; 19(5):405-406.

Karjalainen, S. et al. Salivary cholesterol of healthy adults in relation to serum cholesterol concentration and oral health. J Dent Res. 1997; 76(10):1637-1643.

Katona, I. et al. PMP22 expression in dermal nerve myelin from patients with CMT1A. Brain. 2009; 132(Pt 7):1734-1740.

Li, J. et al. Skin biopsies in myelin-related neuropathies: bringing molecular pathology to the bedside. Brain. 2005; 128(Pt 5):1168-1177.

Meyer zu Horste, G. et al. Antiprogesterone therapy uncouples axonal loss from demyelination in a transgenic rat model of CMT1A neuropathy. *Ann Neurol*. (2007); 61(1):61-72.

Nave, K. A. et al., Mechanisms of disease: inherited demyelinating neuropathies. Nat Clin Pract Neurol. 2007; 3(8): 453-464.

Niebrój-Dobosz, I. et al. Serum lipids in various polyneuropathies. Neurol Neurochir Pol. 197711(4):421-426

Niemann, A. et al. Pathomechanisms of mutant proteins in Charcot-Marie-Tooth disease. Neuromolecular Med. 2006; 8(1-2):217-242.

Passage, E. et al. Ascorbic acid treatment corrects the phenotype of a mouse model of CMT disease. Nature Med. 2004; 10(4): 396-401.

Patroclo, C. B. et al. Autosomal dominant HMSN with proximal involvement: new Brazilian cases. Arquivos de Neuro-Psiquiatria. 2008; 67(3B):892-896

Sahenk, Z. et al. NT-3 promotes nerve regeneration and sensory improvement in CMT1A mouse models and in patients. Neurology. 2005; 65(5):681-689.

Sereda, M. et al. A transgenic rat model of Charcot-Marie-Tooth disease. *Neuron*. (1996); 16(5): 1049-60.

Sereda, M. W. et al. Therapeutic administration of progesterone antagonist in a model of Charcot-Marie-Tooth disease (CMT-1A). Nat Med 2003; 9: 1533-1537.

Shy, M. E. et al. Reliability and Validity of the CMT Neuropathy Score as a Measure of Disability. *Neurology* 2005; 64 (7): 1209-14.

Suter, U. & Scherer, S. S. Disease mechanisms in inherited neuropathies. Nat. Rev. Neurosci. 2003; 4: 714-726.

Soukhova, N. et al. Isotope dilution tandem mass spectrometric method for T4/T3. Clin Chim Acta. (2004);343(1-2):185-90.

Syrjänen, S. M. et al. Free amino acid levels in oral fluids of normal subjects and patients with periodontal disease. Arch Oral Biol. 1990; 35(3):189-193.

Venta, R. et al. Year-Long Validation Study and Reference Values for Urinary Amino Acids Using a Reversed-Phase HPLC Method. Clinical Chemistry. 2001; 47: 575-583

Weiner, D. S. et al. The Akron dome midfoot osteotomy as a salvage procedure for the treatment of rigid pes cavus: a retrospective review. J Pediatr Orthop. 2008; 28(1):68-80.

Yamashita, K. et al. Highly sensitive determination of estrone and estradiol in human serum by liquid chromatography-electrospray ionization tandem mass spectrometry. *Steroids* (2007); 72: 819-827.

Yao, J. K. et al. Lipid abnormalities in hereditary neuropathystar: Part 2. Serum phospholipids. Journal of the Neurological Sciences. 1978; 36(2):225-236.

Young, P. et al. Treatment for Charcot-Marie-Tooth disease. Cochrane Database Syst Rev. 2008; (1): CD006052.

The invention claimed is:

1. An in vitro method for determining a response to a treatment of Charcot-Marie-Tooth disease 1A (CMT1A) in a human subject having CMT1A and undergoing said treatment, and for determining the treatment, wherein said method comprises treating said human subject with a combination of: (a) baclofen or a salt thereof, (b) naltrexone or a salt thereof, and (c) sorbitol or a salt thereof, and:
   i) quantifying the level(s) of alanine or tryptophan, or both, in a biological sample from said human subject during the treatment,
   ii) comparing the level(s) of alanine or tryptophan, or both, measured in step i) to level(s) of alanine and/or tryptophan, respectively, measured previously in the same human subject before the beginning of the treatment, or at an earlier stage of said treatment, wherein an increase of at least 5% in the level(s) of alanine and/or tryptophan is indicative of an improvement of CMT1A disease, and
   iii) continuing administering said treatment when an increase of at least 5% in the level(s) of alanine and/or tryptophan is determined in step ii) or adapting the treatment to said human subject when the treatment is determined to provide no improvement in CMT1A disease in step ii).

2. The method of claim 1, wherein said biological sample is a fluid biological sample.

3. The method of claim 1, wherein said biological sample is a blood sample.

4. The method of claim 1, wherein the method comprises:
   i) quantifying the levels of alanine and tryptophan in the biological sample from said human subject, and
   ii) comparing the levels of alanine and tryptophan measured in i) to the levels of alanine and tryptophan measured previously in the same human subject.

5. The method of claim 1, wherein the human subject having CMT1A has received the treatment with baclofen, naltrexone and sorbitol for three months.

6. The method of claim 1, the method further comprising adapting the treatment of a human subject having levels of alanine and tryptophan that are lower after being treated with a combination of: i) baclofen or a salt thereof, ii) naltrexone or a salt thereof, and iii) sorbitol or a salt thereof by administering increased amounts of: i) baclofen or a salt thereof, ii) naltrexone or a salt thereof, and iii) sorbitol or a salt thereof to said human subject.

7. The method of claim 1, wherein the alanine and/or tryptophan level(s) from step i) and the previous alanine and/or tryptophan level(s) are measured at a time interval of 2 months or more.

8. The method of claim 7, wherein the level(s) of alanine and/or tryptophan measured previously is/are measured before any treatment for CMT1A or at an early stage of the treatment for CMT1A.

9. The method of claim 1, wherein the step (i) of measuring tryptophan and/or alanine levels is made in conjunction with at least one additional diagnostic test or marker for CMT1A, the additional diagnostic test or marker selected from protein, physiological, neurophysiological, genetic, behavioral, electrophysiological, clinical or phenotypical.

10. The method of claim 9, wherein said at least one additional diagnostic test is the clinical test selected from Charcot-Marie-Tooth Neuropathy Score (CMTNS) or Overall Neuropathy Limitations Scale (ONLS).

11. The method of claim 9, wherein said at least one additional diagnostic test or marker is the physiological test or marker selected from 6MWT, 9HPT, Ankle Dorsiflexion or Grip.

12. The method of claim 9, wherein said at least one additional diagnostic test is the electrophysiological test selected from Compound muscle action potential (CMAP) or Motor conduction velocity (MCV).

* * * * *

UNITED STATES PATENT AND TRADEMARK OFFICE
CERTIFICATE OF CORRECTION

PATENT NO. : 9,945,876 B2
APPLICATION NO. : 14/755466
DATED : April 17, 2018
INVENTOR(S) : Daniel Cohen, Ilya Chumakov and Serguei Nabirochkin Page 1 of 1

It is certified that error appears in the above-identified patent and that said Letters Patent is hereby corrected as shown below:

In the Specification

Column 13,
Line 20, "CYBSB" should read --CYB5B--.

Column 21,
Line 34, "(CMTNS) < 20" should read --(CMTNS) ≤ 20--.

Signed and Sealed this
Thirtieth Day of April, 2019

Andrei Iancu
*Director of the United States Patent and Trademark Office*